United States Patent [19]

Merkenschlager et al.

[11] Patent Number: 4,766,325
[45] Date of Patent: Aug. 23, 1988

[54] METHOD FOR TESTING FOR FAULTY PLATED-THROUGH BORES CIRCUIT BOARDS

[75] Inventors: Hans-Hermann Merkenschlager, Augsburg; Friedrich Kraus, Adelsried; Gergely Szolnoki, Augsburg, all of Fed. Rep. of Germany

[73] Assignee: Siemens Aktiengesellschaft, Berlin and Munich, Fed. Rep. of Germany

[21] Appl. No.: 74,908

[22] Filed: Jul. 17, 1987

[30] Foreign Application Priority Data

Jul. 18, 1986 [DE] Fed. Rep. of Germany ....... 3624379

[51] Int. Cl.$^4$ .............................................. G01N 21/88
[52] U.S. Cl. ...................................... 250/572; 356/241
[58] Field of Search ....................... 356/430, 431, 241; 250/571, 572

[56] References Cited

U.S. PATENT DOCUMENTS 3,785,738 1/1974 Hoppke ................................ 250/572
3,812,348 5/1974 Cippke ................................ 250/572

FOREIGN PATENT DOCUMENTS 0111404 6/1984 European Pat. Off. .

*Primary Examiner*—David C. Nelms
*Assistant Examiner*—Crystal Cooper
*Attorney, Agent, or Firm*—Hill, Van Santen, Steadman & Simpson

[57] ABSTRACT

A method for testing for faultily plated-through bores in printed circuit boards by means of a light transmitter on one side of the respective bore and a receiver at the other side which receives light which penetrates through voids of the plated-through bore. An annular opening is formed around the bore to be evaluated, being applied after the plating-through and the depth thereof being slightly less than the thickness of the printed circuit board. The annular opening is illuminated. The light penetrating through the bore then indicates voids at which a faulty plating-through was carried out.

3 Claims, 1 Drawing Sheet

METHOD FOR TESTING FOR FAULTY PLATED-THROUGH BORES CIRCUIT BOARDS

BACKGROUND OF THE INVENTION

This invention relates generally to methods for checking for faultily plated-through bores in printed circuit boards and, in particular, to a method for checking for faultily plated-through bores by means of a light transmitter on one side of the respective bore and a receiver on the other side, which receives light penetrating through voids of the plated-through bore.

In order to check printed circuit boards for faultily plated-through bores, typically specimens are removed from a group of printed circuit boards and are laterally ground until half of the bores are removed. At the other side, the board is ground off up to about 1 mm from the hole walls. Utilizing a light source, light is then directed onto the bore at this opposite side and the potential light penetration is observed on the opposite side, thus, indicating occurring pores or voids in the metallization.

In this method, however, the printed circuit board to be tested must be destroyed and the preparation of the specimen takes considerable time.

European patent application No. 111 404 discloses the use of a light transmitter arranged at one side of the bore and the light receiver arranged at the other side. The bore to be tested is covered at the light transmitter side, and only light passing through potential pores or voids in the plate-throughs is then received by means of a light receiver.

This testing method, however, is not suitable for multi-layer printed circuit boards or structured printed circuit boards, since the respective metal layer would hinder the light passage. Moreover, this testing method can only be carried out after the conclusion of the manufacturing process.

SUMMARY OF THE INVENTION

It is an object of the present invention to create a testing method which allows a testing for faulty plate-throughs in plate-through multi-layered printed circuit boards before structuring the outer layers and without taking a sample.

In order to achieve this objective, the present invention proceeds such that annular openings are applied around the bore to be evaluated. The annular opening is formed after the plating-through of the bore and the depth of the annular opening are slightly less than the thickness of the printed circuit board. The annular openings are then illuminated.

Obtained as a result of these measures is a testing method which can be fully integrated into the manufacturing sequence, whereby the manufacturing through-put time is considerably shortened. Moreover, this method allows the entire bore to be observed instead of half of the bore as in the prior art methods, whereby the reliability of the evaluation is increased. Moreover, the sample to be tested remains in the circuit board specimen, so that the fault allocation is likewise simplified as a result thereof. Moreover, this method can be employed both for multi-layered printed circuit boards and for structured printed circuit boards.

BRIEF DESCRIPTION OF THE DRAWINGS

The features of the present invention which are believed to be novel, are set forth with particularily in the appended claims. The invention, together with further objects and advantages, may best be understood by reference to the following description taken in conjunction with the accompanying drawings, in the several figures of which like reference numerals identify like elements, and in which:

FIG. 1 is a cross-sectional view of a plated-through bore in a printed circuit board depicting the method of detecting voids in the plating-through.

DESCRIPTION OF THE PREFERRED EMBODIMENT

Figure 1:
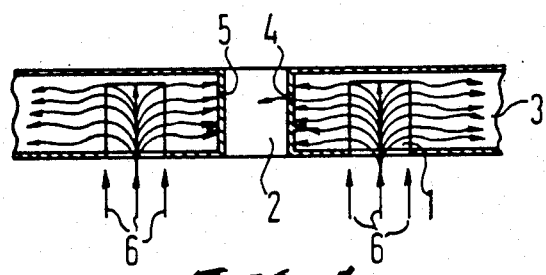
Figure 2:
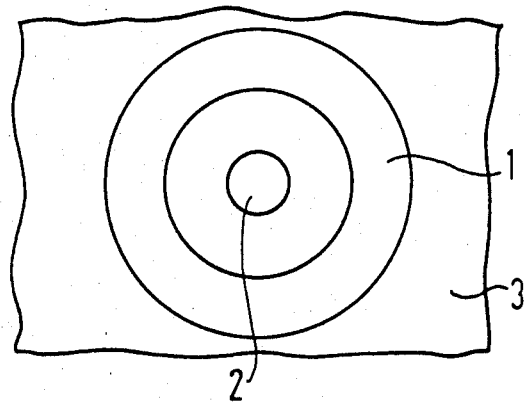
FIG. 2 is a top view of the FIG. 1 plated-through bore in the printed circuit board showing the annular opening.

The present invention has general applicably, but is most advantageously utilized for measuring for faultily plated-through bores in a printed circuit board. Depicted in FIGS. 1 and 2 is a portion of a printed circuit board 3 in the proximity of a plated-through bore 2. An annular opening 1 is introduced all around the bore 2, which is provided with a continuous metallization 5. The annular opening 1 may be formed by, for example, a crown bit and the depth of the annular opening 1 is slightly less than the thickness of the printed circuit board 3. The annular opening 1 is illuminated with a light source 6 (shown by arrows in FIG. 1). The light then penetrates into the bore 2 through voids 4 after traversing through the printed circuit board 3. The light traversing through the voids 4 can be detected with a light receiver (not shown).

The invention is not limited to the particular details of the apparatus depicted, and other modifications and applications are contemplated. Certain other changes may be made in the above described apparatus without departing from the true spirit and scope of the invention herein involved. It is intended, therefore, that the subject matter in the above depiction shall be interpreted as illustrative and not in a limiting sense.

What is claimed is:

1. A method for testing for faultily plated-through bores in a printed circuit board by means of a light transmitter at the one side of the respective bore and a receiver at the other side of the respective bore which receives light penetrating through the voids of the plated-through bore, comprising:
    applying an annular opening around the bore to be evaluated after the plating-through, the depth of said bore being slightly less than the printed circuit board thickness; and
    illuminating said annular opening.

2. A method for testing for faultily plated-through bores in a printed circuit board by means of a light transmitter at the one side of the respective bore and a receiver at the other side of the respective bore which receives light penetrating through the voids of the plated-through bore, comprising:
    forming an annular opening around the bore to be evaluated to a depth slightly less than the printed circuit board thickness;
    illuminating only said annular opening; and
    receiving light penetrating voids of the plated-through bores.

3. A method for testing for faultily plated-through bores in a printed circuit board comprising:
    forming an annular opening in a first side of the printed circuit board around a selected bore to be evaluated to a depth slightly less than the printed board thickness;

providing a light transmitter on a first side of the printed circuit board;

illuminating with said light transmitter only said annular opening;

providing a light receiver; and detecting light penetrating voids of the plated-through bore with said light receiver.

* * * * *